(12) United States Patent
Cichocki, Jr. et al.

(10) Patent No.: US 7,887,746 B2
(45) Date of Patent: Feb. 15, 2011

(54) RAPID THERMAL TREATMENT FOR COLORING SURGICAL NEEDLES

(75) Inventors: Frank Richard Cichocki, Jr., Easton, PA (US); David Demarest, Parsippany, NJ (US); Gregory Hollin, Yardley, PA (US); Eugene D. Reynolds, Avon by the Sea, NJ (US)

(73) Assignee: Ethicon, Inc., Somerville, NJ (US)

( * ) Notice: Subject to any disclaimer, the term of this patent is extended or adjusted under 35 U.S.C. 154(b) by 301 days.

(21) Appl. No.: 11/956,120

(22) Filed: Dec. 13, 2007

(65) Prior Publication Data
US 2009/0151823 A1 Jun. 18, 2009

(51) Int. Cl.
*C21D 1/00* (2006.01)
*C21D 1/74* (2006.01)

(52) U.S. Cl. .................. 266/252; 219/653; 219/654; 148/559; 148/576; 148/582; 148/625; 148/633; 148/634

(58) Field of Classification Search ............ 148/277, 148/284–287, 559, 576, 582, 625, 633, 634; 219/653, 654; 266/252
See application file for complete search history.

(56) References Cited

U.S. PATENT DOCUMENTS

| | | | |
|---|---|---|---|
| 4,295,033 A * | 10/1981 | Lindgren et al. ............ | 219/388 |
| 4,501,312 A | 2/1985 | Matsutani | |
| 5,415,707 A | 5/1995 | Bendel et al. | |
| 5,630,268 A | 5/1997 | Smith et al. | |
| 5,935,411 A * | 8/1999 | Brown et al. .............. | 205/672 |
| 5,968,394 A | 10/1999 | Schob | |
| 7,001,472 B2 | 2/2006 | Collier et al. | |
| 2008/0147117 A1 | 6/2008 | Cichocki et al. | |
| 2008/0295927 A1 | 12/2008 | Cichocki et al. | |

FOREIGN PATENT DOCUMENTS

| | | |
|---|---|---|
| EP | 0 611 552 | 8/1994 |
| EP | 0646352 | 4/1995 |
| JP | 55 058324 | 5/1980 |
| JP | 2002 143172 | 5/2002 |

* cited by examiner

*Primary Examiner*—Roy King
*Assistant Examiner*—Lois Zheng
(74) *Attorney, Agent, or Firm*—Roberts Mlotkowski Safran & Cole, P.C.

(57) ABSTRACT

An apparatus for thermally treating and coloring a plurality of curved suture needles. The apparatus includes a conveyer for transferring the plurality of curved suture needles from a source of curved suture needles to a receiver, a housing positioned adjacent the conveyer, the housing having a first end, a second end, and an opening running from the first end to the second end, the opening aligned with the conveyer to enable the plurality of curved suture needles to pass therethrough, a heat source located within the housing for heating the plurality of curved suture needles as the plurality of curved suture needles are transferred by the conveyer from the first end of the housing to the second end of the housing and a system for providing a gas mixture containing a fractional concentration of oxygen to oxidize and colorize the surfaces of the plurality of curved suture needles as the plurality of suture needles pass through the housing. A process for thermally treating and coloring a plurality of curved suture needles to colorize and enhance the stiffness and yield moment of the curved suture needles is also provided.

8 Claims, 7 Drawing Sheets

200
RAPID THERMAL TREATMENT FOR COLORING SURGICAL NEEDLES

FIELD OF THE INVENTION

The present invention relates to an apparatus and process for producing suture needles having a desirable surface coloration. More specifically, the present invention relates to an apparatus and process for imparting surface coloration to suture needles.

BACKGROUND OF THE INVENTION

Suture needles are often colored to assist a surgeon in visibly distinguishing the needle and visually locating the needle point in the surgical field in which the surgeon is performing a surgery. For example, if the surgical field is filled with fluid it may be difficult for the surgeon to see a silver colored needle against the fluid, or against tissue that is surrounded by fluid such as saline or blood. Moreover, the bright lights commonly used in surgery strongly reflect from silver needles, producing a glare that compounds the difficulty of seeing the point of the surgical needle. Additionally, certain surgeries, particularly coronary artery bypass surgery, necessarily involve the use of suture needles of small diameter, which are difficult to visually distinguish in the surgical field due to their small size. In response to the need to visibly distinguish the suture needle from the surgical field, stainless steel needles have been colored black using coloration processes that may require toxic chrome bearing solutions. In addition to the special handling procedures that must be implemented when using these chrome bearing solutions, they also pose an environmental hazard and considerable care must be taken in their disposal.

When utilizing suture needles having small diameters, it is desirable for such needles to have exceedingly high bending stiffness and strength. In particular, surgery of this type requires that the path of the suture needle be closely controlled. If the needle flexes excessively as it enters the tissue or as it pierces the inner surface of a blood vessel before re-emerging, improper placement of the needle and serious trauma to the tissue and the patient may possibly occur. In use, suture needles may be subjected to significant stressing forces to overcome frictional drag through the tissue. These forces resisting needle penetration often occur in patients undergoing cardiovascular surgery who exhibit calcified or toughened tissue due to coronary artery disease. In these procedures, the suture needle must be able to pass through not only the blood vessel, but also any hard calcified tissue that may be located along the periphery of the blood vessel lumen. An overly compliant needle may deflect elastically during tissue penetration and may result in a loss of placement control. As such, it is preferable that the needle should have a relatively high bending stiffness, that is, a low tendency to flex and high tendency to retain its configuration when subjected to a deforming force. Hence, stiffness in bending is a desirable property for the handling and performance of suture needles. A stiff needle resists elastic deflection and can thus be directed as intended to provide a high level of control.

Thus, there is a need for suture needles that exhibit high robust surface coloration, particularly for surgical procedures that require small diameter needles.

SUMMARY OF THE INVENTION

In one aspect, provided is an apparatus for thermally treating and coloring a plurality of curved suture needles. The apparatus includes a conveyer for transferring the plurality of curved suture needles from a source of curved suture needles to a receiver, a housing positioned adjacent the conveyer, the housing having a first end, a second end, and an opening running from the first end to the second end, the opening aligned with the conveyer to enable the plurality of curved suture needles to pass therethrough, a heat source located within the housing for heating the plurality of curved suture needles as the plurality of curved suture needles are transferred by the conveyer from the first end of the housing to the second end of the housing and a system for providing a gas mixture containing a fractional concentration of oxygen to oxidize and colorize the surfaces of the plurality of curved suture needles as the plurality of suture needles pass through the housing.

In another aspect, provided is a process for thermally treating and coloring a plurality of curved suture needles to colorize and enhance the stiffness and yield moment of the curved suture needles. The process includes the steps of conveying the plurality of curved suture needles from a source of curved suture needles to a receiver, heating the plurality of curved suture needles to a temperature below the recrystallization temperature of the curved suture needles as the plurality of curved suture needles pass between the source of curved suture needles to the receiver, providing a gas mixture containing a fractional concentration of oxygen and coloring the surfaces of the plurality of curved suture needles as the plurality of suture needles pass through the gas mixture containing a fractional concentration of oxygen as the plurality of suture needles are heated.

In one embodiment, the system for providing a gas mixture containing a fractional concentration of oxygen substantially prevents excessive heat transfer to the conveyer.

In another embodiment, a first guide for positioning the plurality of curved suture needles is provided to substantially center the plurality of curved suture needles within the opening of the housing, the first guide for positioning the plurality of curved suture needles located between the housing and the source of curved suture needles.

In yet another embodiment, the conveyer includes a strip or plurality of strips to which the plurality of curved suture needles are attached.

In still yet another embodiment, the plurality of curved suture needles is adhesively attached to the strip or plurality of strips.

In a further embodiment, the plurality of curved suture needles is welded to the strip or plurality of strips.

In a still further embodiment, a second guide for positioning the plurality of curved suture needles is provided to substantially center the plurality of curved suture needles within the opening of the housing, the second guide for positioning the plurality of curved suture needles located between the housing and the receiver.

These and other advantages, features and attributes of the disclosed apparatus and processes and their advantageous applications and/or uses will be apparent from the detailed description that follows, particularly when read in conjunction with the figures appended hereto.

DETAILED DESCRIPTION OF THE INVENTION

Definitions

Figure 1:
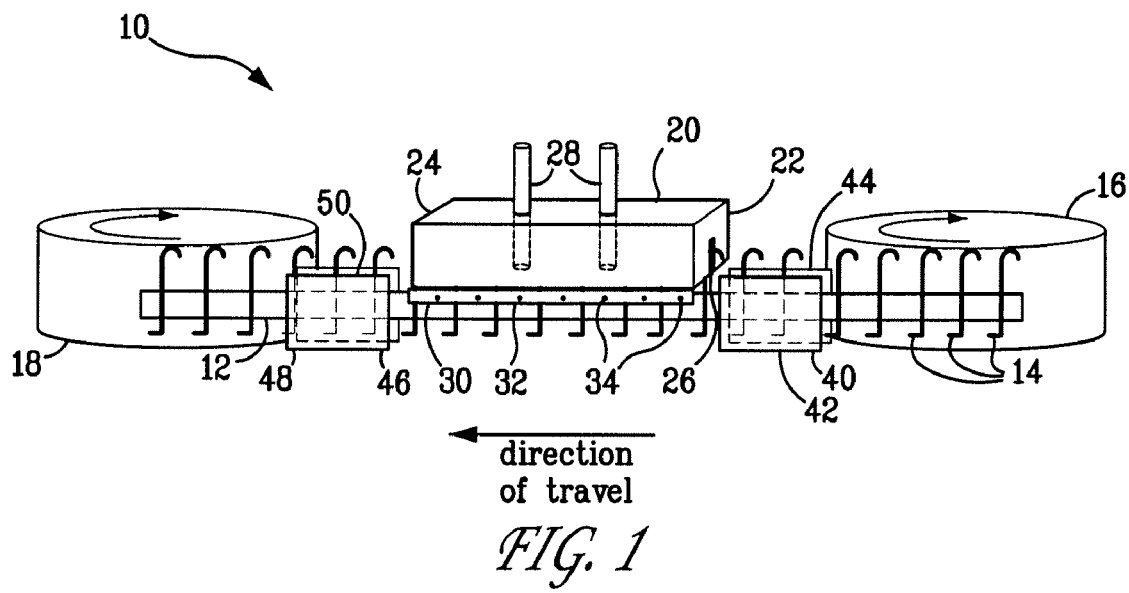
FIG. 1 is a schematic representation of an apparatus for thermally treating and coloring a plurality of curved suture needles, in accordance herewith.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, "bending stiffness" (stiffness in bending) means the resistance to elastic deformation of a curved suture needle.

As used herein, "diameter" herein is meant the square root of $(4A/\pi)$, wherein A is the cross-sectional area.

As used herein, "ductile-to-brittle-transition-temperature" (DBTT) means the temperature above which a substantial improvement in ductility of an alloy occurs. When used herein, the DBTT is determined as the temperature at which the alloy exhibits at least 5% elongation to break in a tensile test.

As used herein, "ductility" is the ability of an alloy to withstand plastic deformation without breaking.

As used herein, "elastic deformation" is the deformation, strain, or displacement that is recoverable by removing the applied load.

As used herein, "elongation-to-break" is a measurement of sample percent elongation in a simple tension test used to assess alloy ductility.

As used herein, an "I-beam needle body" refers to any variety of needle body designs that incorporate flattened opposed sides, instead of an entirely round design.

As used herein, "material properties" means the properties of the material only, derived by testing in a manner in which needle shape and surface properties do not influence data. Examples include: Young's modulus, ultimate tensile strength (when tested in simple tension), and microhardness hardness.

As used herein, a "needle blank" is an elongate piece of wire, a portion of which is converted via multiple processes into the shape of a suture needle. Also, as used herein, "needle blank" refers to a portion of wire extending from the proximal end of the suture needle used to move and position the suture needle for processing in accordance herewith.

As used herein, "recrystallization temperature" is the temperature at which new grains will form in the microstructure of an alloy.

As used herein, "simple tension" is the tension applied in one dimension, with other dimensions being unconstrained.

As used herein, "thermal forming" means the plastic forming conducted on a heated work piece.

As used herein, "ultimate bending moment" means the greatest moment applied to a needle during bend testing conducted under ASTM Standard F-1840-98a.

As used herein, "yield bending moment" means the amount of moment required to initiate plastic deformation during bend tests conducted under ASTM standard F-1840-98a.

Reference is now made to FIGS. 1-8B, wherein like numerals are used to designate like parts throughout.

Referring now to FIGS. 1-4, an apparatus 10 for thermally treating and coloring a plurality of curved suture needles 14 is shown. The apparatus includes a conveyer 12 for transferring the plurality of curved suture needles 14 from a source of curved suture needles 16 to a receiver 18. Conveyer 12 may be formed from a strip comprised at least in part of metal, paper, or plastic, wherein mechanical attachment may be achieved by bending a preformed tab (not shown) connected to a metal strip around at least a portion of each of the plurality of curved suture needles 14 or, alternatively, a pressure sensitive adhesive may be coated on at least one surface of the paper, plastic, or metal carrier strip, or, alternatively, at least one weld is utilized to affix each of the plurality of curved suture needles 14 to the metal carrier strip.

Apparatus 10 also includes a housing 20 positioned adjacent conveyer 12. Housing 20 includes a first end 22, a second end 24 and an opening 26 extending from first end 22 to second end 24. As shown, opening 26 is aligned with conveyer 12 to enable the plurality of curved suture needles 14 to pass through housing 20.

Housing 20 also includes a heat source 28 located within housing 20 for heating the plurality of curved suture needles 14 as the plurality of curved suture needles 14 are transferred by conveyer 12 from the first end 22 of housing 20 to the second end 24 of housing 20. Heat source 28 may be a conventional heat source and may include one or more electrical resistance heating elements, one or more inductively coupled heating elements, a hot gas stream, or the like. By employing a narrow opening 26 for needle 14 passage, excessive radiative heat transfer to the conveyer 12 is minimized or prevented. To further enhance the ability of housing 20 to minimize or prevent excessive radiative heat transfer to conveyer 12, housing 20 may also employ insulative material (not shown) within its interior and/or on its exterior surfaces.

Figure 2:
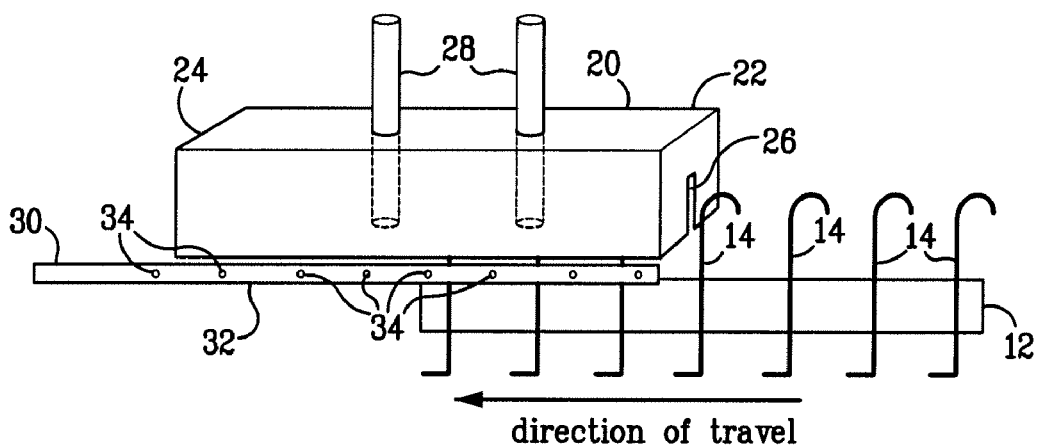
FIG. 2 is a schematic representation of a heat source for use in an apparatus for thermally treating and coloring a plurality of curved suture needles, in accordance herewith.
Figure 4:
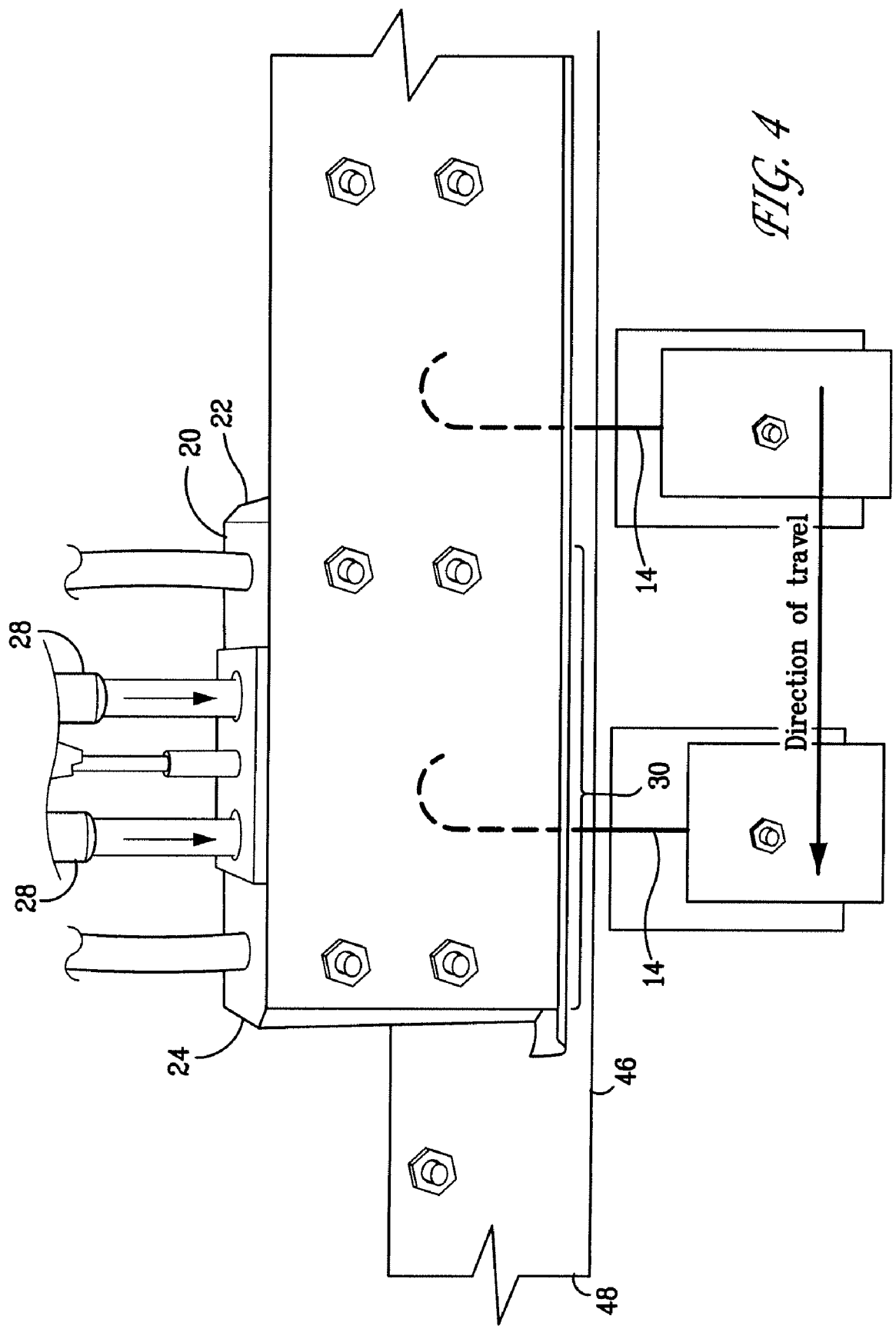
FIG. 4 shows one form of an apparatus for thermally treating and coloring a plurality of curved suture needles, focusing on a heat source and guide means, in accordance herewith.

As shown in FIGS. 1, 2 and 4, apparatus 10 may further include a system for providing a gas mixture 30, the gas mixture containing a fractional concentration of oxygen to oxidize and colorize the surfaces of the plurality of curved suture needles 14 as the plurality of suture needles 14 pass through the housing 20. The system for providing a gas mixture 30 may include a gas supply wand 32 having a plurality of ports 34 for emitting the gas mixture containing a fractional concentration of oxygen. The system for providing a gas mixture 30 may advantageously substantially prevent excessive heat transfer to the conveyer 12.

As shown in FIGS. 1 and 4, apparatus 10 may also include a guide 40 for positioning the plurality of curved suture needles to substantially center the plurality of curved suture needles 14 within opening 26 of housing 20. In one embodiment, apparatus 10 includes a first guide 40 for positioning the plurality of curved suture needles 14 to substantially center the plurality of curved suture needles 14 within opening 26 of housing 20. As shown, first guide 40 for positioning the plurality of curved suture needles 14 is located between housing 20 and the source of curved suture needles 16. In one embodiment, first guide 40 for positioning the plurality of curved suture needles 14 may include a first plate 42 and a second plate 44, positioned in a spaced parallel relationship. In another embodiment, apparatus 10 may also include a second guide 46 for positioning the plurality of curved suture needles 14 to substantially center the plurality of curved suture needles 14 as they exit opening 26 of housing 20. As shown, second guide 46 for positioning the plurality of curved suture needles 14 is located between housing 20 and the receiver 18. Second guide 46 for positioning the plurality of curved suture needles 14 may include a first plate 48 and a second plate 50, positioned in a spaced parallel relationship.

Figure 3:
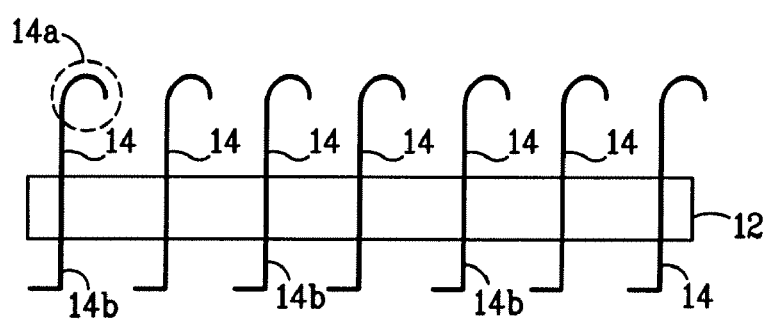
FIG. 3 is a schematic representation of a plurality of curved suture needles attached to a carrier strip, in accordance herewith.

As shown in FIG. 1, in one embodiment, the source of curved suture needles 16 includes a pay-off spool. In another embodiment, receiver 18 includes a take-up spool. As shown in FIG. 3, each of the plurality of curved suture needles 14 may include a curved suture needle portion 14a and a needle blank 14b. Needle blank 14b has utility in that it may be affixed to conveyer 12, as described hereinabove.

In another embodiment, provided is a process for thermally treating and coloring a plurality of curved suture needles 14 to colorize and enhance the stiffness and yield moment of the curved suture needles 14. The process comprising includes steps of conveying the plurality of curved suture needles 14 from a source of curved suture needles 16 to a receiver 18, heating the plurality of curved suture needles 14 to a temperature below the recrystallization temperature of the curved suture needles 14 as the plurality of curved suture needles 14 pass between the source of curved suture needles 16 to the receiver 18, and providing a gas mixture containing a fractional concentration of oxygen and coloring the surfaces of the plurality of curved suture needles 14 as the plurality of suture needles 14 pass through the gas mixture containing a fractional concentration of oxygen as the plurality of suture needles is heated 14.

In one embodiment, the curved suture needles 14 are heated to a temperature ranging from about 350 to about 900° C. in an oxidizing atmosphere, in order to impart a robust adherent black, blue, or yellow oxide surface coating to the tungsten alloy suture needle described herein. Exposure time may range from seconds to several minutes, depending upon the temperature or temperatures may range from about 400 and about 1000° C. for duration of about 1 second to about 5 minutes. Examples of an oxidizing atmosphere include, but are not limited to, oxygen-rich atmosphere, air, or a carbon dioxide/carbon monoxide gas mixture that decomposes or reacts with the tungsten alloy surface to form an oxide.

In another embodiment, the curved suture needles 14 may first be heated to a temperature ranging from about 350 to about 1900° C. in an inert or reducing atmosphere, followed by heating to a temperature ranging from about 350 to about 900° C. in an oxidizing atmosphere, to impart improved bending stiffness and a robust adherent black, blue, or yellow surface coating to the tungsten alloy suture needles.

As will be described in more detail below, in one embodiment, the plurality of curved suture needles 14 includes a tungsten alloy. In another embodiment, the plurality of curved suture needles 14 includes at least one or more metals selected from the group consisting of rhenium, tantalum or molybdenum. In yet another embodiment, the plurality of curved suture needles 14 includes up to 30 weight percent rhenium and the balance tungsten.

In one embodiment, the process disclosed herein is a rapid continuous process wherein the mechanism for stiffness and yield moment enhancement is selected from one of the following: 1) stress relief, 2) martensitic transformation and stress relief, 3) precipitation strengthening and stress relief and 4) tempering and stress relief. In one embodiment, the curved suture needles 14 are comprised of a tungsten alloy, a steel alloy, or a molybdenum alloy.

The mechanism of stress relief, alone, may be applied to tungsten alloys, molybdenum alloys, and certain austenitic steel alloys such as 302 SS, 304 SS, 316 SS, 4310 SS and the like. The mechanism of matensitic transformation plus stress relief may be applied to certain martensitic steels such as alloy 420 SS. Precipitation strengthening plus stress relief may be applied to martensitic-aged stainless steels such as 455 SS, 465 SS. Tempering plus stress relief may be applied to martensitic and some martensitic-aged steels, with particular application to 420 SS.

It is important to note that, certain stainless steels are prone to embrittlement via the formation of chrome carbides or sigma phase when heat treated for durations of several minutes or more in the temperature range of about 400 to about 1000° C. This may be particularly true of the austenitic stainless steels listed above. The continuous heat treatments described herein may prevent the formation of these embrittling phases by rapidly processing at higher temperatures where these embrittling phases are not thermodynamically prone to formation, or by not allowing sufficient time for formation or growth of these embrittling phases.

As indicated above, the suture needles may be formed from an alloy of tungsten. The tungsten alloy may comprise one or more metals selected from the group consisting of rhenium, osmium, tantalum, or molybdenum. In one embodiment, the alloy may be a tungsten-rhenium alloy, and has no more than trace amounts of other elements present. The metal other than tungsten may be present in an amount up to about 30 weight percent of the alloy, or in an amount ranging from about 20 to about 26 weight percent of the alloy.

The suture needle may have a diameter effective to permit satisfactory usage in fine surgery. Typically, the diameter will be less than about 60 mils (thousandths of an inch), or less than about 15 mils, down to about 1 mil, or about 1.4 to about 12 mils. It will be recognized that the suture needle may have a circular body cross-section, and that the needle may also be of a non-circular cross-sectional shape such as triangular; trapezoidal; rectangular; hexagonal; elliptical; or rectangular wherein the opposed shorter ends of the rectangle are rounded into semicircles. The needle may be provided with a "ribbon" shape with a single set of opposing flat sides, or a rectangular or "I-beam" shape, or with a cross-section which smoothly undergoes transition from the point to a circular cross-section, to a rectangular cross-section having rounded and then sharper corners, as described in U.S. Pat. No. 4,799,484, the contents of which are herein incorporated by reference in their entirety.

The suture needle may be straight or curved, but the improvement in bending strength and stiffness disclosed and achieved herein is especially advantageous for curved needles. In one embodiment, the needle is curved through a radius of curvature, which need not be constant but is preferably constant. Thus, shapes of the needles disclosed herein include sections of a circle, such as a quarter circle, three-eighths circle, half circle, or five-eighths of a circle.

Following the final drawing of the tungsten alloy or stainless steel wire to the final desired diameter, one end of the needle is given a point having the desired shape, the point being provided by any conventional technique such as grinding. Optionally, the body may be formed by pressing or grinding operations into the variety of shapes. The needle may then be given its desired curvature, typically by rolling around a mandrel of the desired radius of curvature. The opposite end of the needle is given an opening in its end, or other means by which the end of a suture can be attached to the needle by swaging or the like.

In order to impart improved bending strength and stiffness to the suture needle described herein, particularly after a curvature has been imparted to the needle, the curved needle is heated to a temperature below the recrystallization temperature of the tungsten alloy. In one embodiment, the suture needle is heated to a temperature ranging from about 350 to about 1900° C. In another embodiment, the suture needle is heated to a temperature ranging from about 400 to about 1650° C. for about 1 second to about 5 minutes to impart bending stiffness to the surgical needle.

Advantageously, as described above, the curved suture needles 14 are attached to a conveyer material and passed in the vicinity of a heat source 28. In this way, the exposure time to elevated temperature is limited, since higher temperatures for shorter periods of time are effective to achieve the desired stiffening effect.

The curved suture needles 14 produced as described herein may also be provided with a coating, for instance, a polymeric coating, in accordance with known techniques, if desired. The needle is then attached to the suture, packaged and sterilized, again in accordance with conventional techniques.

The curved suture needles 14 produced as described herein are characterized by a desirable combination of bending stiffness, strength and ductility. For the curved suture needles 14 produced as described herein, the wire tensile yield strength is generally at least about 250,000 ksi. High wire tensile yield strength is useful as it indicates the ability of the needles to withstand potentially deforming stresses without suffering permanent deformation.

The wire from which the curved suture needles 14 are made also exhibits uniquely high Young's modulus of elasticity, generally at least about 400 GPa. The high Young's modulus is desirable in that it reflects the potential for higher stiffness and the ability of the curved suture needles 14 produced as described herein to withstand potentially deforming stresses by retaining their shape, without undue flexing. However, in practice, as described above, a high Young's modulus of the wire alone does not directly translate into a high bending stiffness for a curved suture needle 14. Indeed to capitalize on the intrinsic material stiffness, a heat treatment is applied to the curved suture needles 14, as described hereinabove.

Both needle bending strength and needle bending stiffness influence handling characteristics, as well as penetration performance and efficacy of the suture needle. It is important to note that in almost all circumstances, the suture needle should be used in applications where the yield bend moment is not exceeded, since above this value, the needle may bend plastically, may lose its original shape, and may no longer function as intended. It is thus apparent that a desirable characteristic of a suture needle is a high yield bend moment, which is a manifestation of the bending strength of the suture needle. Below the yield bend moment, the resistance of bending of the suture needle is best characterized by the needle bending stiffness.

Needle bending stiffness is a critical measure of the resistance to elastic or recoverable bending of the suture needle before needle deflection reaches the yield bend angle and can be calculated as the yield bend moment divided by the yield bend angle. If a straight or curved suture needle has a low value of bending stiffness, substantial bending of the needle may occur for a given bend moment, whereas if a straight or curved suture needle exhibits a high bending stiffness value, relatively little elastic bending of the needle will occur for a given bend moment. Surgeons tend to perceive a high degree of elastic bending as a loss of control or as poor penetration performance since the needle point is not translating directly with the motion of their hands. As such, needle bending stiffness may be recognized as an important measure of needle performance in most surgical applications.

The following examples are provided for purposes of illustration and should not be interpreted as limiting in any way the scope of the claims appended hereto.

EXAMPLES

Example 1

ASTM standard F1840-98a (Reapproved 2004) provides standard terminology for surgical suture needles and ASTM standard F1874-98 (Reapproved 2004) provides details of a standard test method for bend testing of needles used in surgical sutures. Both ASTM standards are incorporated herein by reference. Two different measures for the strength of surgical suture needles are used, namely, yield bend moment, which is the amount of moment required to initiate plastic deformation during a bend test, and maximum bend moment, which is the greatest moment applied to a needle during a bend test. This later value of maximum bend moment is typically measured at a point where the needle has undergone substantial plastic deformation and is generally higher than the yield bend moment or point at which plastic deformation initiates. The point of deflection at which plastic deformation initiates, or more formally according to ASTM standards, the angle at which the yield bend moment occurs, is referred to as the yield bend angle.

Figure 5:
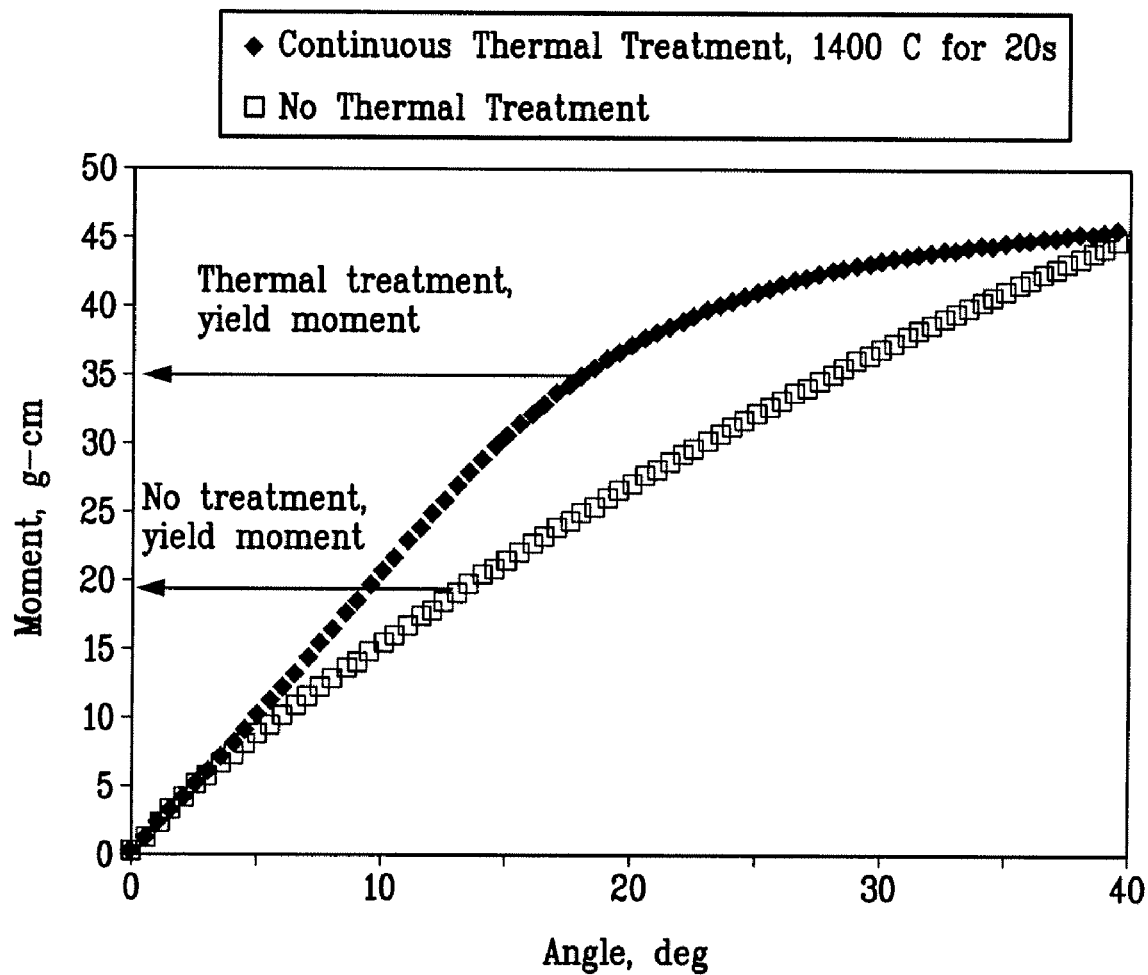
FIG. 5 is a graph comparing the bending performance of a 0.008" diameter curved suture needle produced from a tungsten 26% rhenium alloy that has been subjected to a continuous rapid thermal treatment at 1400° C. for 20 seconds compared to an equivalent tungsten 26% rhenium alloy suture needle that has received no thermal treatment.

A graph comparing the bending performance of a heat treated curved 0.008" diameter suture needle produced from a tungsten 26% rhenium alloy that has been subjected to a continuous rapid thermal treatment at 1400° C. for 20 seconds is compared to an equivalent tungsten 26% rhenium alloy suture needle that has received no thermal treatment is provided in FIG. 5.

All tests were conducted according to ASTM standard F1874-98. The yield bend moment and yield bend angle are marked on the graph. The slope of the tungsten-rhenium alloy suture needle up to the yield bend moment represents bending stiffness and is markedly greater than that provided by the equivalent untreated tungsten 26% rhenium alloy. The heat treatment applied to the tungsten alloy suture needle was conducted under an argon 2% hydrogen atmosphere at 1400° C. for 20 seconds.

Example 2

Figure 6:
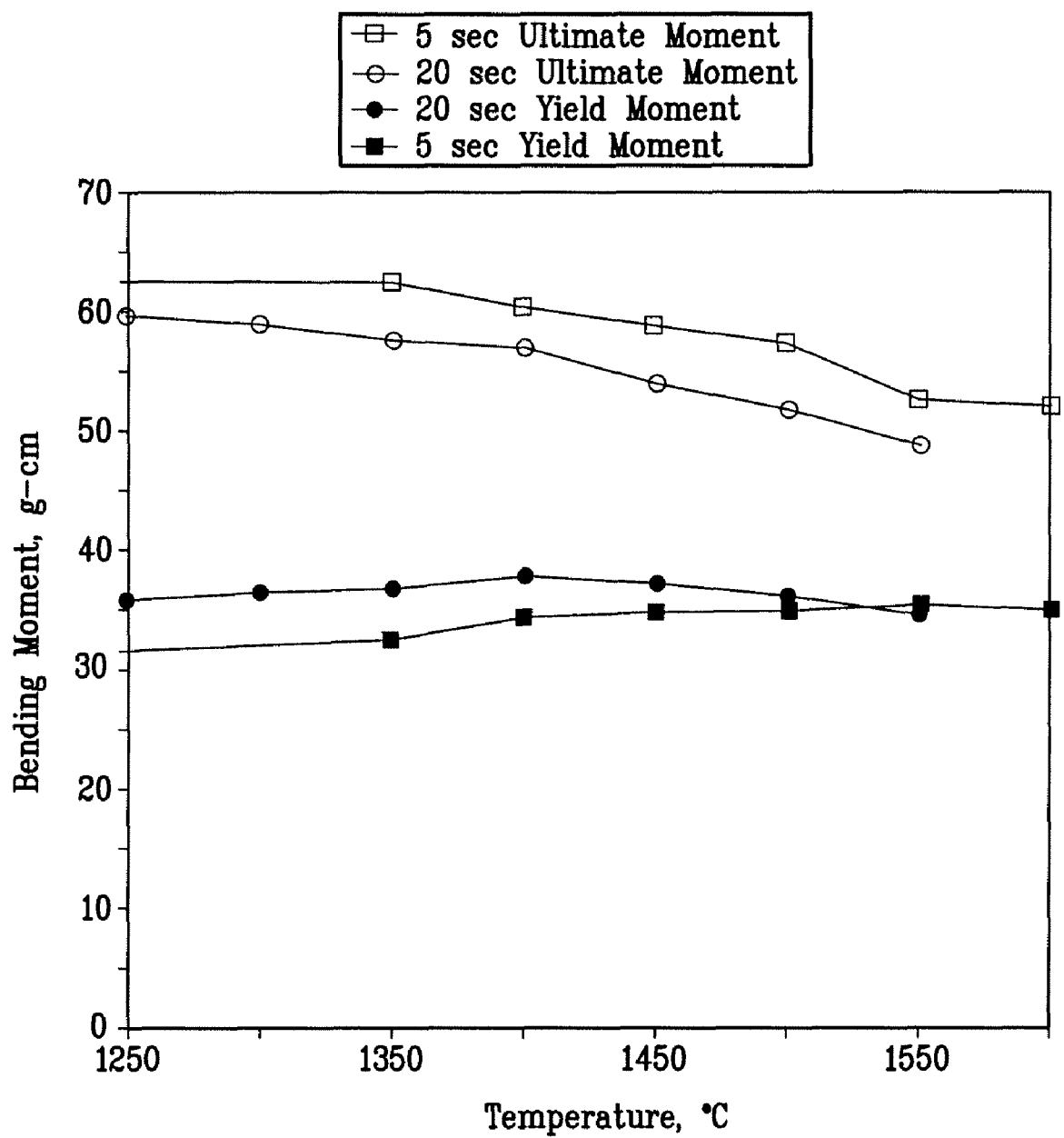
FIG. 6 is a graph showing the effect of temperature and time on yield moments and ultimate moments of a 0.008" diameter curved suture needle produced from a tungsten 26% rhenium alloy.

A graph showing the effect of temperature and time on yield moments and ultimate moments of a 0.008" diameter curved suture needle produced from a tungsten 26% rhenium alloy is presented in FIG. 6. Rapid thermal treatment was conducted at durations of 5 and 20 seconds over a broad temperature range under argon 2% hydrogen gas to maintain an inert non-oxidizing atmosphere. All tests were conducted according to ASTM standard F1874-98. A marked increase in bending stiffness and yield moment occurs with the application of heat treatment with yield moments in excess 30 g-cm vs. the more typical 20 g-cm for equivalent untreated needles of the same size and composition.

Example 3

Figure 7A:
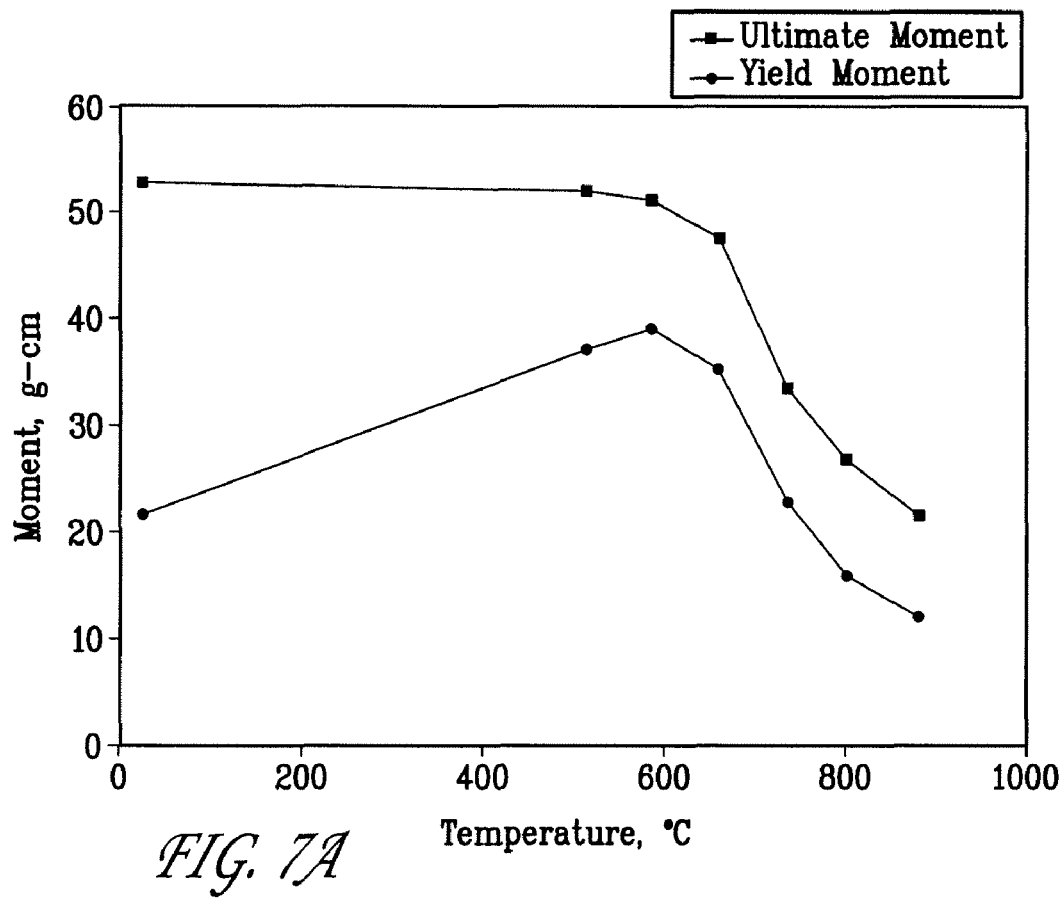
FIG. 7A shows the influence of temperature applied over 20 seconds on the yield moment and ultimate moment of 0.008" diameter curved suture needles produced from austenitic alloy stainless steel series 4310.
Figure 7B:
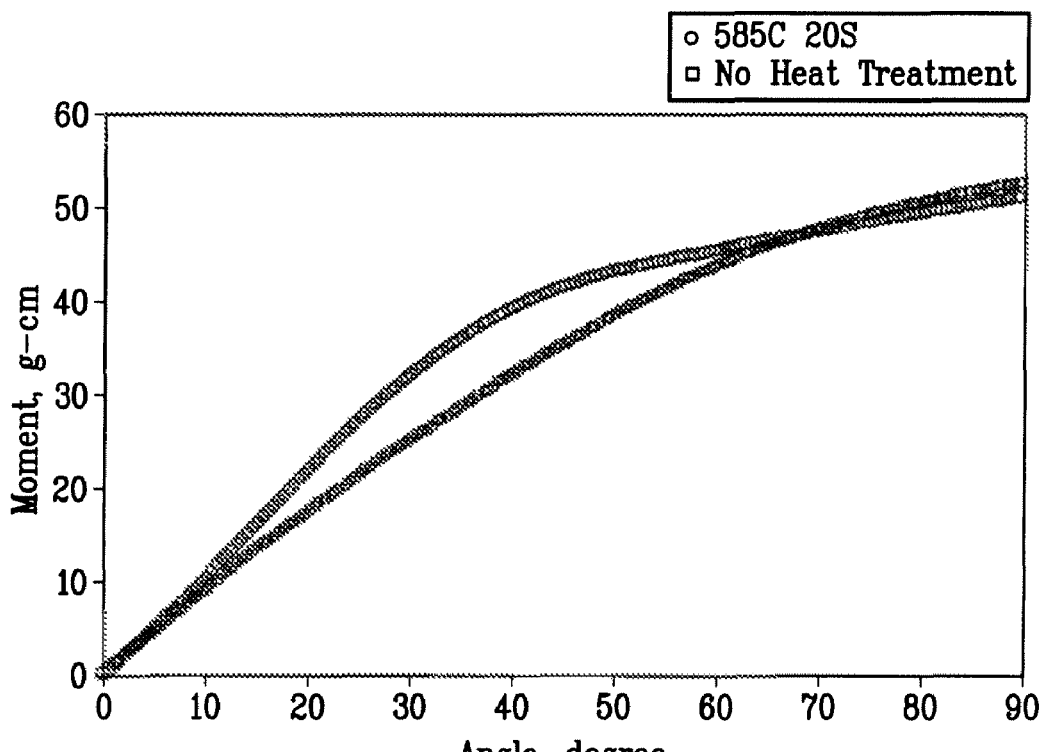
FIG. 7B shows a comparison of bending performance for a stainless steel series 4310 alloy needle, with and without rapid heat treatment.

FIG. 7A shows the influence of temperature applied over 20 seconds on the yield moment and ultimate moment of 0.008" diameter curved suture needles produced from austenitic alloy stainless steel series 4310. FIG. 7B shows a comparison of bending performance for a stainless steel series 4310 alloy needle, with and without rapid heat treatment in accordance herewith. All tests were conducted in substantial accordance with ASTM standard F1874-98.

Example 4

Figure 8A:
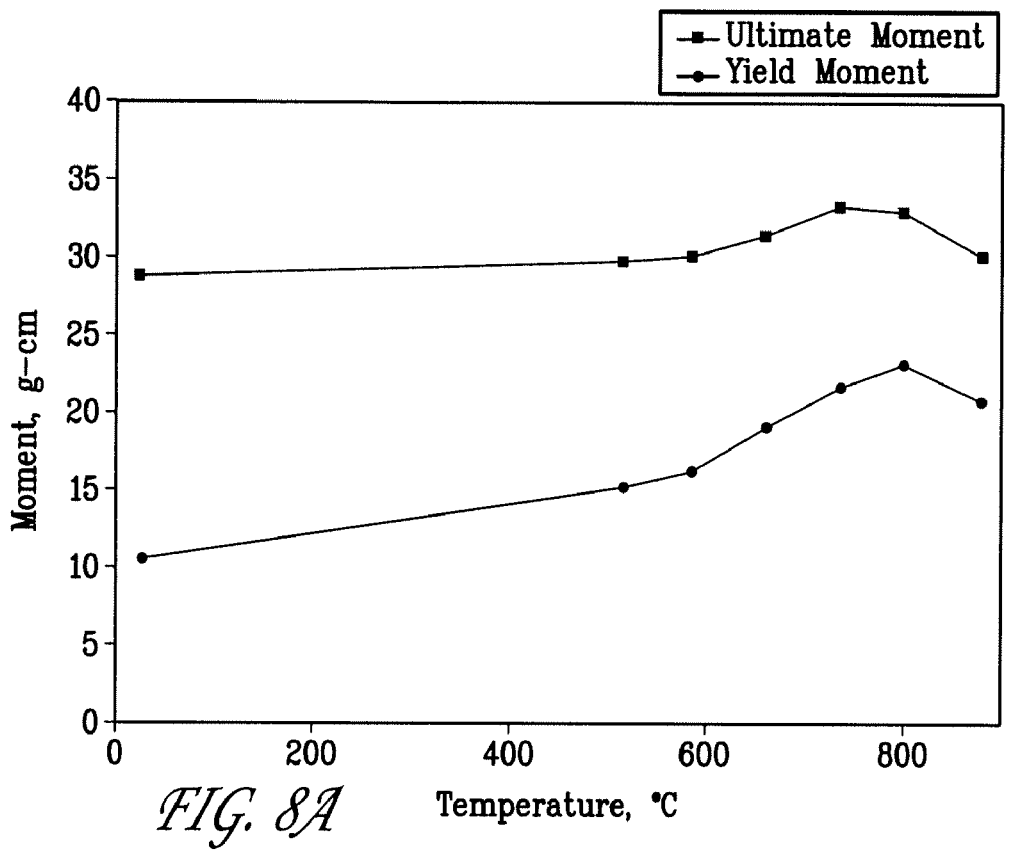
FIG. 8A shows the influence of temperature applied over 20 seconds on the yield moment and ultimate moment of 0.008" diameter curved suture needles produced from a martensitic-aged stainless steel.
Figure 8B:
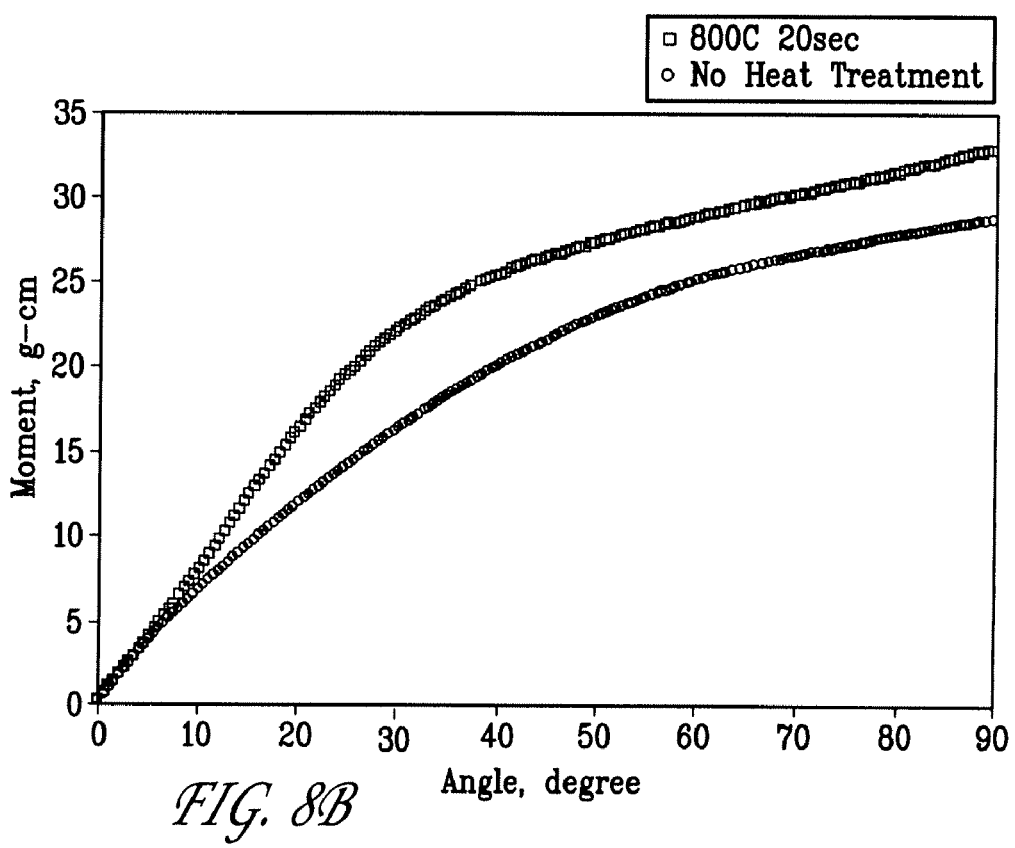
FIG. 8B shows a comparison of bending performance for a martensitic-aged stainless steel needle, with and without rapid heat treatment.

FIG. 8A shows the influence of temperature applied over 20 seconds on the yield moment and ultimate moment of 0.008" diameter curved suture needles produced from a martensitic-aged stainless steel. FIG. 8B shows a comparison of bending performance for a martensitic-aged stainless steel needle, with and without rapid heat treatment. All tests were conducted in substantial accordance with ASTM standard F1874-98. The composition of this martensitic-aged stainless steel was nominally 12% Cr, 9% Ni, 3% Mo, 2% Ti with the balance Fe and trace elements.

Figure 9:
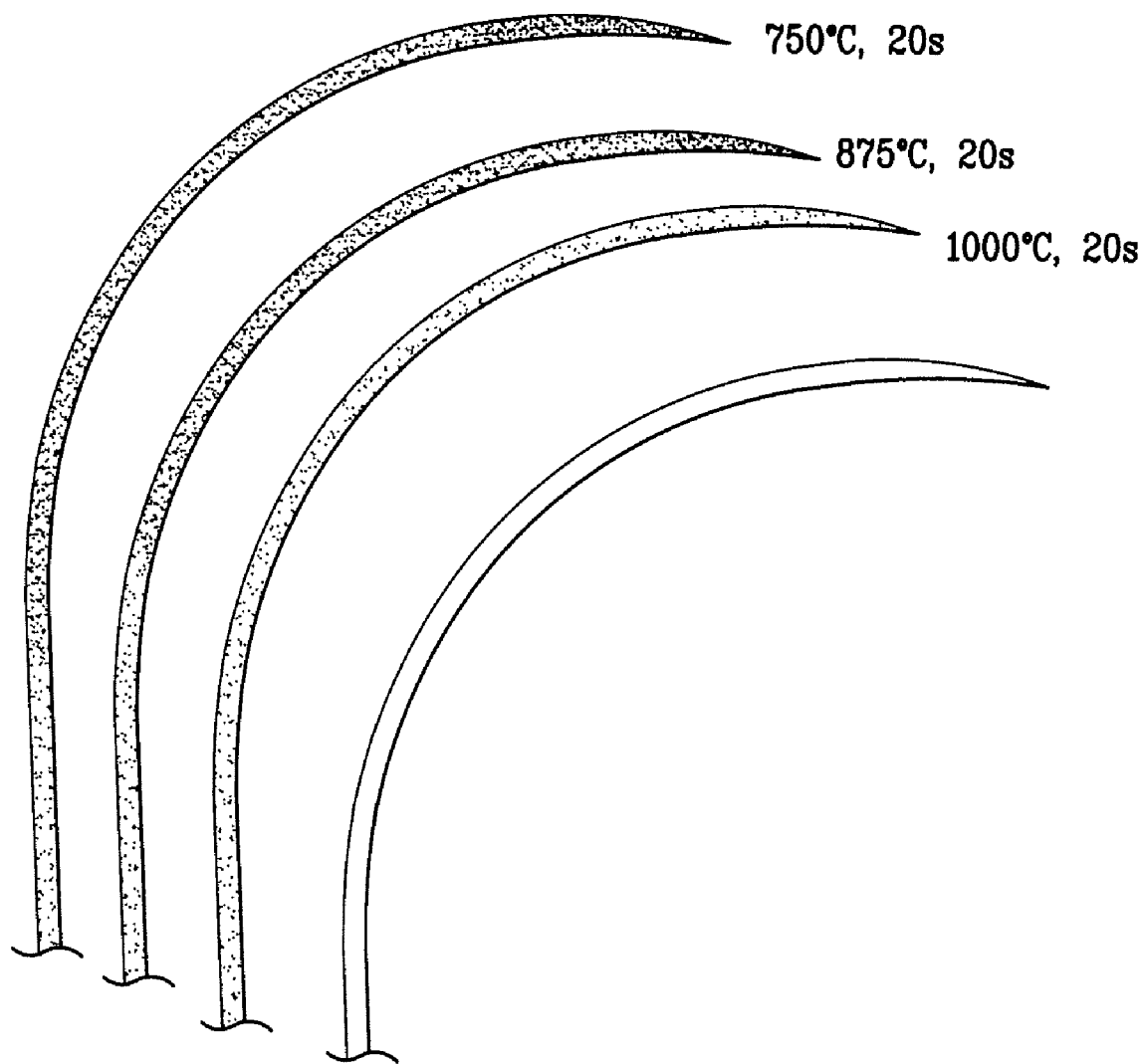
FIG. 9 presents a series of curved suture needles treated and colorized in accordance herewith.

As shown in FIG. 9, the rapid continuous thermal treatment of the type disclosed herein is useful to color or blacken tungsten alloy suture needles in an oxygen bearing atmosphere via the formation of a colored surface oxide. All needles were processed in air without the use of inert shielding gasses for a total duration of 20 seconds using the apparatus schematically depicted in FIG. 4. Temperatures between 750 and 1000° C. yielded needles with a black surface non-reflective surface.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

What is claimed is:

1. An apparatus for thermally treating and coloring a plurality of curved suture needles, the apparatus comprising:
    a) a conveyer for transferring the plurality of curved suture needles from a source of curved suture needles to a receiver;
    b) a housing positioned adjacent said conveyer, said housing having a first end, a second end, and an opening running from said first end to said second end, said opening aligned with said conveyer to enable the plurality of curved suture needles to pass therethrough;
    c) a heat source located within said housing for heating the plurality of curved suture needles as the plurality of curved suture needles are transferred by said conveyer from said first end of said housing to said second end of said housing;
    d) a system for providing a gas mixture containing a fractional concentration of oxygen to oxidize and colorize the surfaces of the plurality of curved suture needles as the plurality of suture needles pass through said housing;
    e) a first guide, comprising a first plate and a second plate, positioned in a spaced parallel relationship, for positioning the plurality of curved suture needles to substantially center the plurality of curved suture needles within the opening of said housing, said first guide for positioning the plurality of curved suture needles located between said housing and said source of curved suture needles; and
    f) a second guide, comprising a first plate and a second plate, positioned in a spaced parallel relationship, for positioning the plurality of curved suture needles to substantially center the plurality of curved suture needles within the opening of said housing, said second guide for positioning the plurality of curved suture needles located between said housing and said receiver.

2. The apparatus of claim 1, wherein said system for providing a gas mixture containing a fractional concentration of oxygen substantially prevents excessive heat transfer to the conveyer.

3. The apparatus of claim 2, further comprising a guide for positioning the plurality of curved suture needles to substantially center the plurality of curved suture needles within the opening of said housing.

4. The apparatus of claim 1, wherein said conveyer comprises a strip or plurality of strips to which the plurality of curved suture needles are attached.

5. The apparatus of claim 4, wherein the plurality of curved suture needles are adhesively attached to the strip or plurality of strips.

6. The apparatus of claim 4, wherein the plurality of curved suture needles are welded to the strip or plurality of strips.

7. The apparatus of claim 4, wherein the source of curved suture needles comprises a pay-off spool.

8. The apparatus of claim 4, wherein the receiver comprises a take-up spool.

* * * * *